United States Patent [19]
Matsuda

[11] Patent Number: 5,608,209
[45] Date of Patent: Mar. 4, 1997

[54] METHOD AND APPARATUS FOR MEASURING MOTION AMOUNT OF A LABORATORY ANIMAL

[75] Inventor: Hideo Matsuda, Funahashi-mura, Japan

[73] Assignee: Toyo Sangyo Co., Ltd., Toyama-ken, Japan

[21] Appl. No.: 363,317

[22] Filed: Dec. 23, 1994

[30] Foreign Application Priority Data

Dec. 27, 1993 [JP] Japan ................................. 5-349770

[51] Int. Cl.$^6$ .............................................. G01V 9/04
[52] U.S. Cl. ................................. 250/221; 119/421
[58] Field of Search ................................. 250/221, 559.4; 119/15, 17; 340/555–557, 573, 574; 356/375

[56] References Cited

U.S. PATENT DOCUMENTS

| | | | |
|---|---|---|---|
| 3,304,911 | 2/1967 | Hakata et al. | 119/15 |
| 3,478,220 | 11/1969 | Milroy | 250/221 |
| 3,805,061 | 4/1974 | De Missimy et al. | 250/221 |
| 4,267,443 | 5/1981 | Carroll et al. | 250/221 |
| 4,337,726 | 7/1982 | Czekajewski et al. | 119/15 |
| 4,384,201 | 5/1983 | Carroll et al. | 250/221 |
| 4,574,734 | 3/1986 | Mandalaywala et al. | 119/15 |
| 4,968,974 | 11/1990 | Sakano | 119/15 |
| 4,998,014 | 3/1991 | Hasegawa | 250/221 |

*Primary Examiner*—Stephone Allen
*Attorney, Agent, or Firm*—Sughrue, Mion, Zinn, Macpeak & Seas

[57] ABSTRACT

An apparatus and method for measuring the motion amount of a laboratory animal. The apparatus includes a main body having a central processing unit therein, and a first and a second frame set to surround a laboratory animal in a bounded area. Each frame includes an optical sensor light-emitting element and an optical sensor light-receiving element. The optical sensor light-emitting element is disposed so as to oppose the optical sensor light-receiving element. The optical sensor light-emitting elements on the first and second frames sequentially emit optical beams such that the light-emitting elements do not emit optical beams at the same time. The light-receiving elements on the first and second frames receive those emitted optical beams which are not obstructed by the laboratory animal so as to detect the location and movements of the laboratory animal. According to the method, the movement amount, complete standing actions, and incomplete standing actions of the laboratory animal are measured via. the optical sensors arranged on the upper and lower frames.

6 Claims, 10 Drawing Sheets

METHOD AND APPARATUS FOR MEASURING MOTION AMOUNT OF A LABORATORY ANIMAL

FIELD OF THE INVENTION

The present invention relates to a method and apparatus for measuring the motion amount of a laboratory animal by detection using optical sensors.

BACKGROUND OF THE INVENTION

Conventionally, a method for detecting a change in dielectric constant caused by the motion of an animal using an LC resonance circuit is adopted in order to measure the motion amount of a laboratory animal.

Also, a method of measuring the motion amount using optical sensors is adopted. However, the conventional methods and apparatuses suffer the following problems.

In the method of detecting a change in dielectric constant caused by a motion of an animal using an LC resonance circuit, when measurements are performed by a plurality of measuring apparatuses, it is actually difficult to maintain each measuring apparatus to the same sensitivity, and the detected dielectric constant is often influenced by the individual difference or action speed of a laboratory animal. In addition, since the detection sensitivity of the apparatus is inversely proportional to a square of the distance to an object to be measured, the detection sensitivity varies depending on the height in a standing posture of a laboratory animal occasionally affecting detected dielectric constant, For this reason, even in a single apparatus, the measurement results vary.

Figure 8:
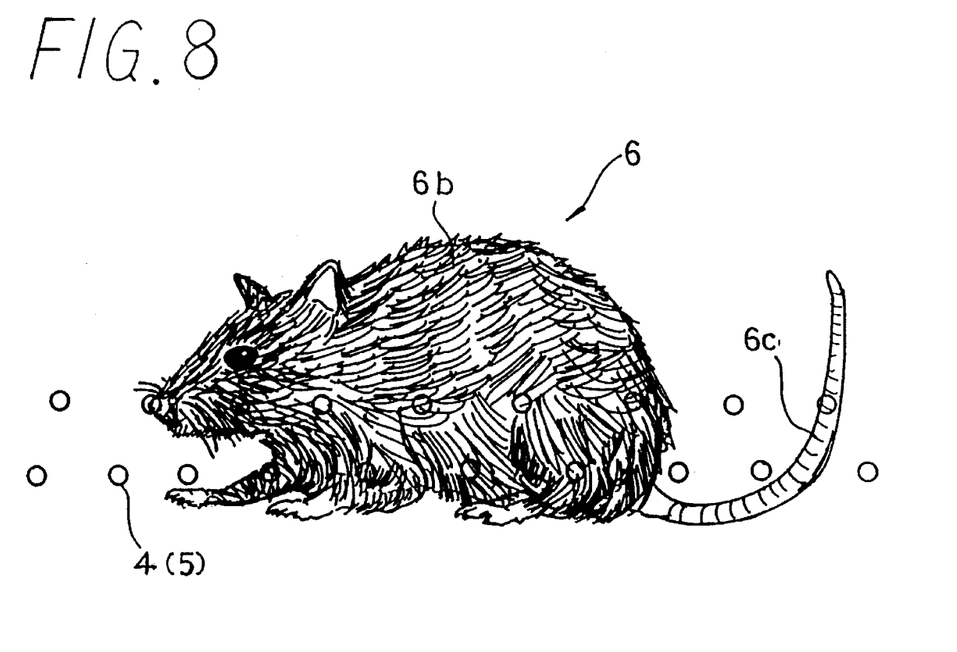
FIG. 8 is a partially enlarged side view of an apparatus according to an embodiment of the present invention, and is an explanatory view showing a state wherein a laboratory animal is in a normal posture.
Figure 9:
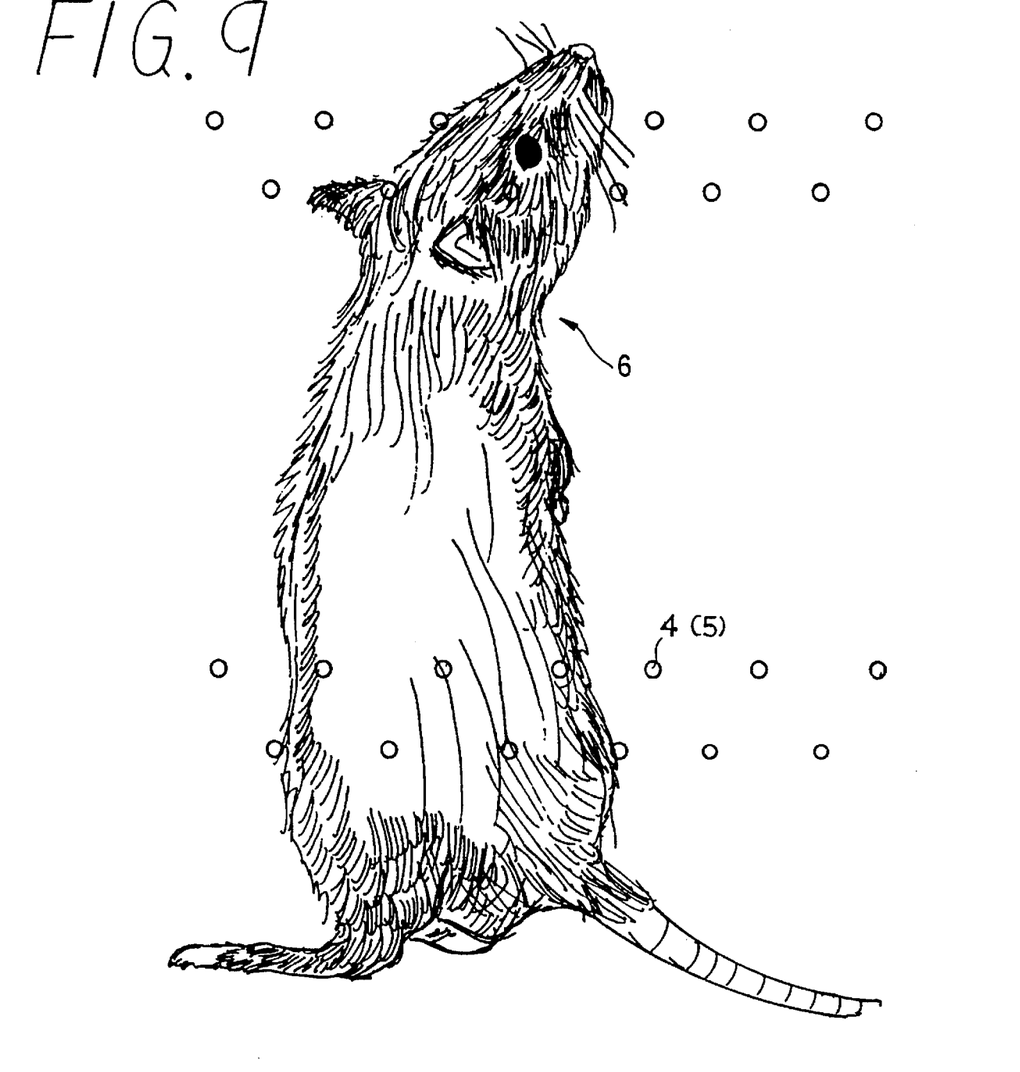
FIG. 9 is a partially enlarged side view of an apparatus according to an embodiment of the present invention, and is an explanatory view showing a state wherein a laboratory animal is in a complete standing posture.
Figure 10:
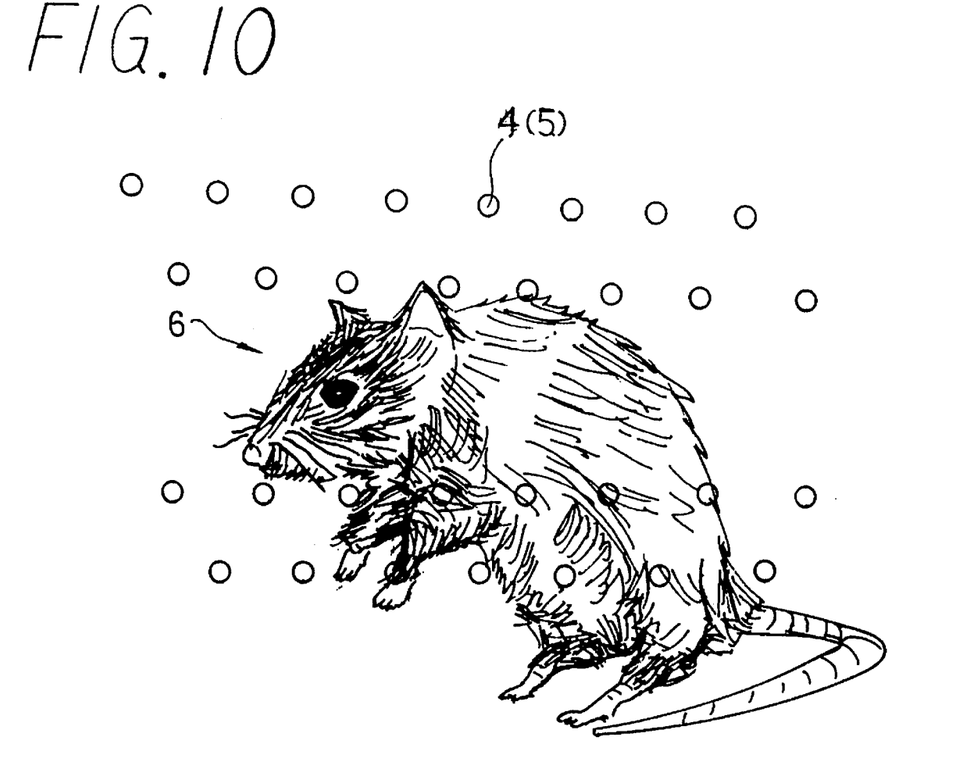
FIG. 10 is a partially enlarged side view of an apparatus according to an embodiment of the present invention, and is an explanatory view showing a state wherein a laboratory animal is in an incomplete standing posture.

When a motion amount is measured using optical sensors, it is difficult to dispose optical sensors at high density in consideration of interferences of light among the optical sensors, and hence, small actions are hardly measured. In particular, a laboratory animal not only merely moves in the horizontal direction but also performs various actions, e.g., a standing action on hind legs at a given position. In this case, the animal may complete a standing action on the hind legs, as shown in FIG. 9 from a normal posture shown in FIG. 8, but sometimes may stay in a lower posture as shown in FIG. 10 and return to the normal posture, and repeat such an action. However, it is difficult for the conventional measuring apparatus using optical sensors to detect such an incomplete standing action as the optical sensors are not arranged at high density, resulting in poor measurement precision of the motion amount.

When a laboratory animal maintains its posture between a complete standing state and an incomplete standing state, a chattering phenomenon, in which the sensor electrically repeats ON and OFF states near an electrical threshold level at which the detection level of the sensor is turned on, occurs due to a delicate change in the animal's posture or an unstable light-shielding state for the optical sensors. This causes the number of times of standing is counted to have an abnormally large value far from an actual value.

Furthermore, in order to eliminate interferences of light among the sensors, light-emitting elements with high focusing characteristics and light-receiving elements with high sensitivity must be used, resulting in an expensive apparatus.

SUMMARY OF THE INVENTION

It is an object of the present invention to provide an inexpensive apparatus and a measuring method thereof for measuring the motion amount of a laboratory animal which are free from a sensitivity difference among apparatuses upon measurement using a plurality of apparatuses, and can conduct repetitive measurements with high precision.

It is another object of the present invention to provide an inexpensive apparatus and a method for measuring the motion amount of a laboratory animal which can accurately measure various actions (e.g., a standing action) of laboratory animals.

An apparatus according to the present invention comprises a main body having a central processing unit (referred to as CPU hereinafter) installed inside, a plurality of frames stacked and set to surround a laboratory animal in a cage or the like, and optical sensor light-emitting elements and optical sensor light-receiving elements arranged on surfaces of the frames so as to correspondingly oppose each other. The optical sensors are controlled by the CPU in the main body. The CPU in the main body also executes correcting and processing input signals detected by the sensors. The light-emitting elements and light-receiving elements are respectively arranged in a staggered pattern. Each light-emitting element adopts a near infrared LED, and each light-receiving element adopts phototransistor.

The plurality of pairs of light-emitting elements and light-receiving elements are arranged at a high density to have an interval of 5 mm or less between neighboring elements. The light-emitting elements are sequentially electrically scanned to emit optical beams and the emitted optical, beams are detected by the corresponding light-receiving elements.

In a method according to the present invention, when detecting the position of a laboratory animal on the horizontal surface using the optical sensors, a length corresponding to an interval between two neighboring optical sensors is added to each of two sides of respective maximum length and maximum width of an area corresponding to the size of the animal which is detected by optical sensors so as to determine the laboratory animal as a rectangular area. The frames are stacked, so that the standing state of the animal is detected by the optical sensors arranged on the upper frame or frames, and the return action from the standing state to the normal posture of the animal is perceived by those arranged on the lower frame or frames, thus counting the number of times of complete standing actions. In addition, when only the area detected by the optical sensors arranged on the lower frame is changed without detection by the optical sensors on the upper frame, such a detection state is counted as an incomplete standing action of the animal.

BRIEF DESCRIPTION OF THE DRAWINGS

FIGS. 7(a) and 7(b) are still another explanatory views of the motion amount measurement process for laboratory animals according to a method in an embodiment of the present invention, in which

DETAILED DESCRIPTION OF THE INVENTION

A motion amount measuring apparatus for laboratory animals according to the present invention comprises a main body having a CPU installed inside, a plurality of frames stacked and set to surround an animal in a cage or the like, and optical sensor light-emitting elements and optical sensor light-receiving elements disposed on a surface of each frame so as to correspondingly oppose each other. In the present invention, the main body preferably has a rectangular planar shape and each frame preferably has a rectangular shape corresponding to the main body. Optical sensor light-emitting elements are preferably arranged on one surface of each of two pairs of opposing surfaces of the frames and optical sensor light-receiving elements are preferably arranged on the other surfaces. Since both the light-emitting elements and the light-receiving elements are fixed to the frame, the optical sensors can be easily handled in units of frames to which the sensors are integrated. The optical sensors can be detached as needed and the optical sensors in the attached state do not particularly require any adjustment. The CPU in the main body executes controlling for electrical scanning of the optical sensors, and correcting and processing input signals detected by the sensors. An output port is provided in the CPU thereby the processed data can be transmitted to a micro computer in order to correct or analyze the measurement data if necessary.

As a plurality of frames are vertically stacked, the standing state of a laboratory animal is detected by the optical sensors of the upper frame or frames, and the return action from the standing state to the normal posture of the animal is detected by the optical sensors of the lower frame or frames, thus counting a single complete standing action. The optical sensors of the lower frame detect the number of times of incomplete standing actions of the animal.

When the light-emitting elements and the light-receiving elements are arranged in a staggered pattern, respectively, the tail of an animal is not detected continuously by the optical sensors. This results the motion of the tail is not measured because the tail is not perceived as an object having a certain area and only a head, trunk and legs of the animal serve as objects to be measured, and the motion amount measurement can be performed with high accuracy.

A plurality of pairs of light-emitting elements and light-receiving elements are arranged at high density to have an interval of 5 mm or less between neighboring elements. The light-emitting elements are sequentially electrically scanned to emit optical beams, and emitted optical beams are received by the corresponding light-receiving elements. Since the light-emitting elements do not emit optical beams simultaneously, interferences of light caused by emission of optical beams from a plurality of optical sensors can be prevented enabling the optical sensors to be arranged at high density. As one optical sensor emits optical beam at a time, the number of amplifiers can be decreased, thereby the manufacturing cost of the apparatus can be reduced.

Interferences of light among optical sensors need not be considered as the light-emitting elements are sequentially electrically scanned to emit optical beams, therefore, the focusing characteristics and the light-receiving sensitivity of the optical sensors become less important. This causes near infrared kEDs and phototransistor as versatile components can be applied as optical sensors and an inexpensive apparatus can be provided. Use of the near infrared kEDs and phototransistor is also advantageous as they do not stimulate a laboratory animal.

Due to high density arrangement of the optical sensors, small actions of a laboratory animal, e.g., an action of forelegs of a rat can be detected.

In a motion amount measuring method for laboratory animals according to the present invention, when detecting the position of the animal on the horizontal surface using the optical sensors, a length corresponding to an interval between two neighboring optical sensors is added to each of two sides of a maximum length and a maximum width of an area corresponding to the size of a laboratory animal which is detected by optical sensors, thus perceiving the size of the animal as a rectangular area. The movement amount $\delta$ of a laboratory animal in the horizontal directions is measured as numerical data calculated by an equation $\delta=\sqrt{(X^2+Y^2)}$ where X and Y indicate the lengthwise and breadthwise movement of the rectangular area on the horizontal surface detected by the optical sensors.

A standing action of an animal is detected by a method to be described below.

When an animal is in a standing posture, the grounding area of the animal on the horizontal surface becomes smaller than that in a normal posture. Such a change in area is detected by the optical sensors of the lower frame. When an animal is in a complete standing posture, the standing state of the animal is also recognized via the optical sensors of the upper frame. Thereafter, when the area of the animal detected by the optical sensors of the lower frame returns from a small area indicating the standing state to the area indicating a normal posture, the return action of the animal from the standing state to the normal posture is recognized, thus counting a single complete standing action.

When an animal makes an incomplete standing action, although the area of the animal detected via the optical sensors of the lower frame becomes small like the complete standing state, however, the animal is not recognized by the optical sensors of the upper frame as the height of the animal in this posture is lower than that in the complete standing state. Therefore, when only the area of the animal detected by the optical sensors of the lower frame changes without being detected by the optical sensors of the upper frame, the number of times of such changes is measured as incomplete standing actions of the animal.

Upon detection of the laboratory animal as a rectangular area, a MOVE1 mask having a relatively small area and a MOVE2 mask having a relatively large area are prescribed to measure the motion amount. The MOVE1 mask sequentially detects small motions of the animal and the MOVE2 mask, large motions of the animal, thus compensating for reliability of measurement. MOVE2 mask is prescribed by adding certain lengths to a size of MOVE1 mask. The added lengths are determined according to an object of a measurement by employing a unit length which is defined from an interval between two neighboring optical sensors.

Since the laboratory animal is detected as a rectangular area, minute actions of animals' body such as breathing, shakes, and the like and the slight light-shielded states caused by animals' hair can be ignored and high-accuracy measurement can be realized.

EXAMPLE

Figure 1:
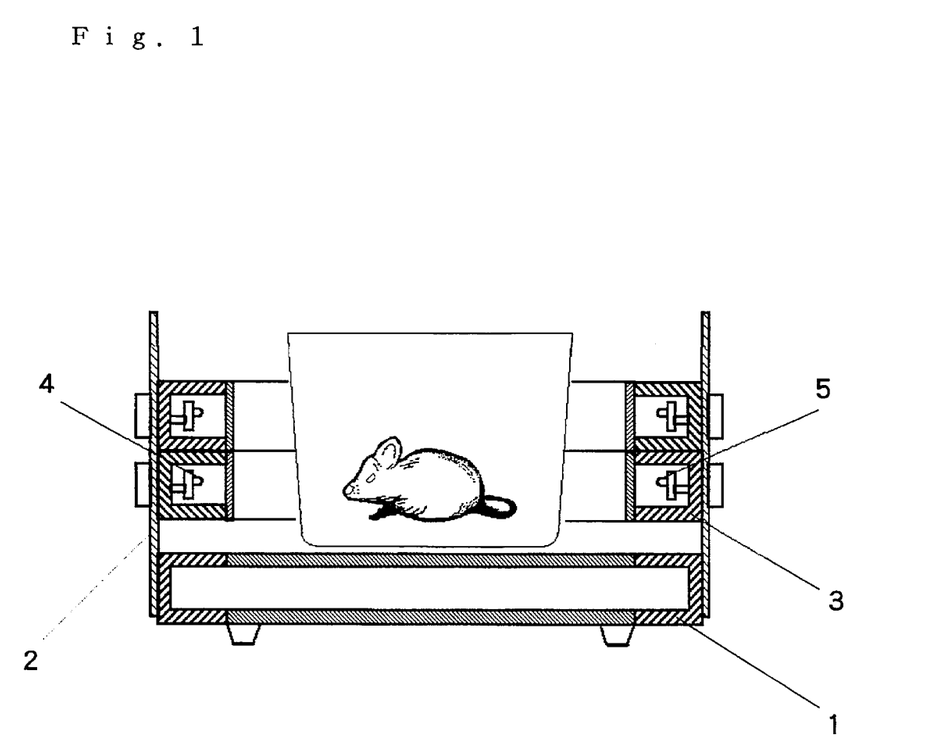
FIG. 1 is a sectional view of a motion amount measuring apparatus for laboratory animals according to an embodiment of the present invention.
Figure 2:
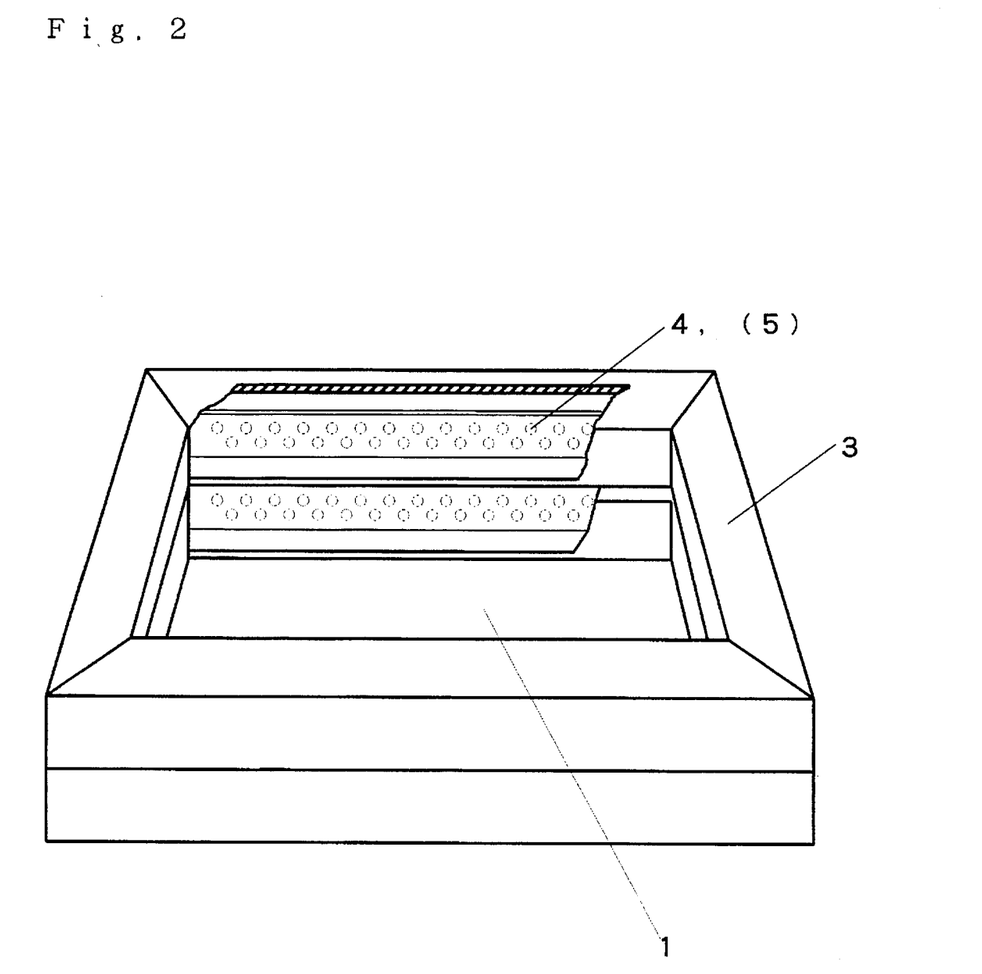
FIG. 2 is a perspective view of the apparatus shown in FIG. 1.

FIG. 1 is a sectional view of a motion amount measurement apparatus for laboratory animals according to an embodiment of the present invention, and FIG. 2 is a perspective view of the apparatus.

As shown in FIGS. 1 and 2, two frames 3 are vertically stacked and fixed to a main body 1 having a rectangular planar shape via side walls 2. In the main body 1, a CPU is installed (not shown) to control the electrical scanning of the optical sensors, and to correct and process input signals by the optical sensors. A plurality of optical sensor light-emitting elements 4 using near infrared LEDs are attached to one surface of each of two pairs of opposing surfaces of respective frame 3, and a plurality of optical sensor light-receiving elements 5 using phototransistors are attached to positions opposing the optical sensor light-emitting elements 4 on the other surfaces.

As shown in FIG. 2, the light-emitting elements 4 and the light-receiving elements 5 are arranged in a staggered pattern, respectively, with keeping an interval of 5 mm between neighboring elements. With this arrangement, as shown in FIG. 8, a tail 6c of an animal 6 is not continuously detected by the optical sensors 4 and 5, and the tail 6c does not serve as a target for motion amount measurement. For this reason, only a head, trunk and legs of the animal 6 serve as actual targets for motion amount measurement, and measurement can be performed with high accuracy.

The light-emitting elements 4 are sequentially electrically scanned to emit optical beams, thereby preventing interferences of light among the optical sensors. This enables the optical sensors to be arranged at high density allowing high-accuracy measurement.

(1) HORIZONTAL MOVEMENT AMOUNT

Figure 3:
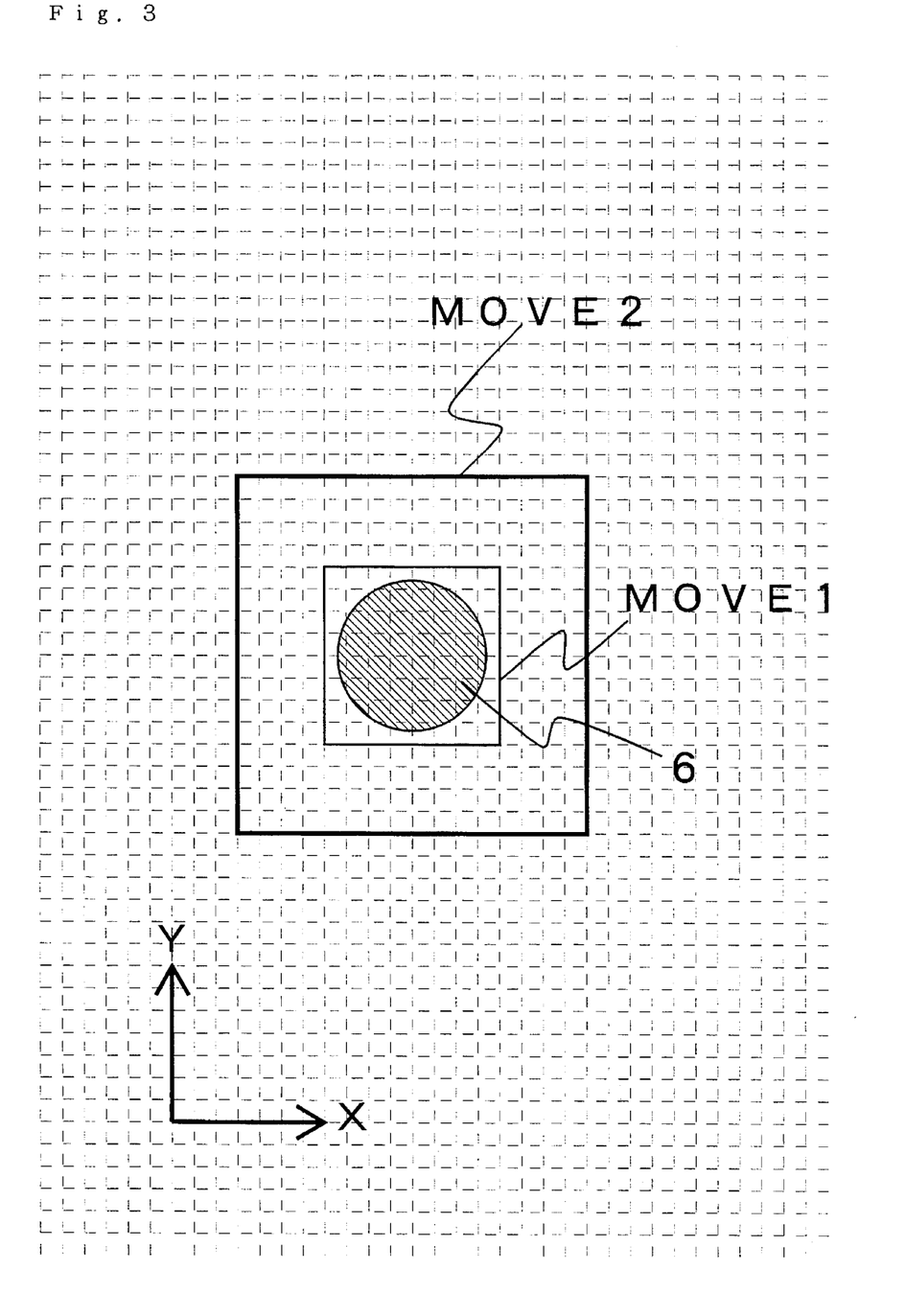
FIG. 3 is an explanatory view of the motion amount measurement process for laboratory animals according to a method in an embodiment of the present invention.

FIGS. 3 to 7 are explanatory views when detecting the position of a laboratory animal on the horizontal surface by the optical sensors. In each of FIGS. 3 to 7, dotted lines represent optical beams emitted from the light-emitting elements 4 and received by the corresponding light-receiving elements 5. A circle 6 represents an area of an animal detected by the optical sensors. In the measurement, as shown in FIG. 3, the current position of an animal on the horizontal surface is detected by the optical sensors, and a length corresponding to an interval between two neighboring optical sensors is added to each of two sides of a maximum length and a maximum width of the detected area 6 of the animal, thereby recognizing the animal as a rectangular area, i.e., a MOVE1 mask. Furthermore, another rectangular area larger than the rectangular area of MOVE1 mask is recognized as a MOVE2 mask.

Figure 4:
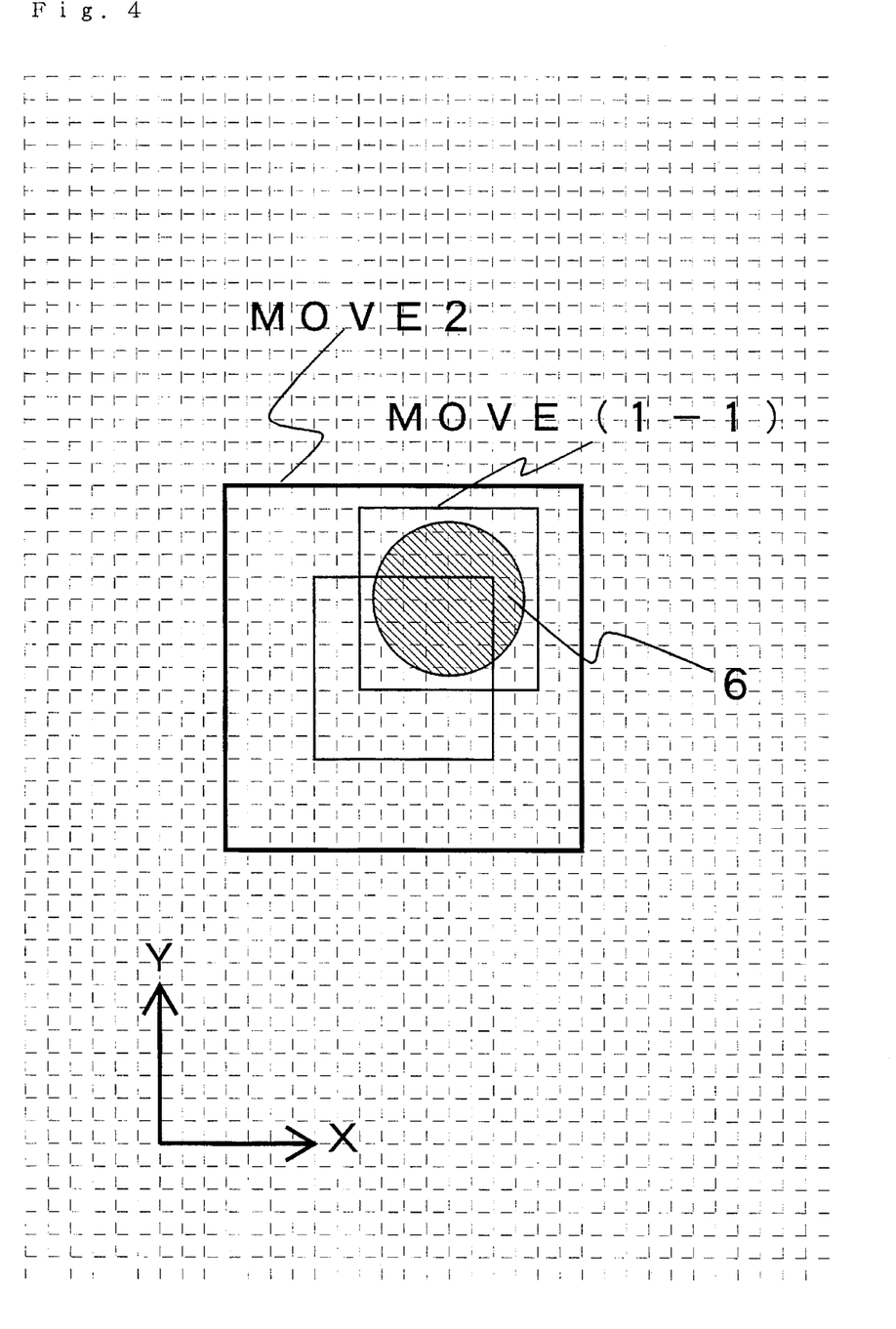
FIG. 4 is another explanatory view of the motion amount measurement process for laboratory animals according to a method in an embodiment of the present invention.

When the animal 6 moves, as shown in FIG. 4, the animal 6 after the movement is recognized as a new MOVE(1-1) mask, and the movement amount is counted. More specifically, the current position and the position before the movement are compared with each other according to the prescription which determines an interval between two neighboring optical sensors as a unit amount, and when a movement defined by X=2 and Y=3 is detected, as shown in FIG. 4, the movement amount is calculated by the following equation:

$$MOVE(1\text{-}1) = \sqrt{(2^2 + 3^2)} = 3.60555 \qquad 1$$

The result of equation 1 is rounded to obtain an amount of "3.6".

Figure 5:
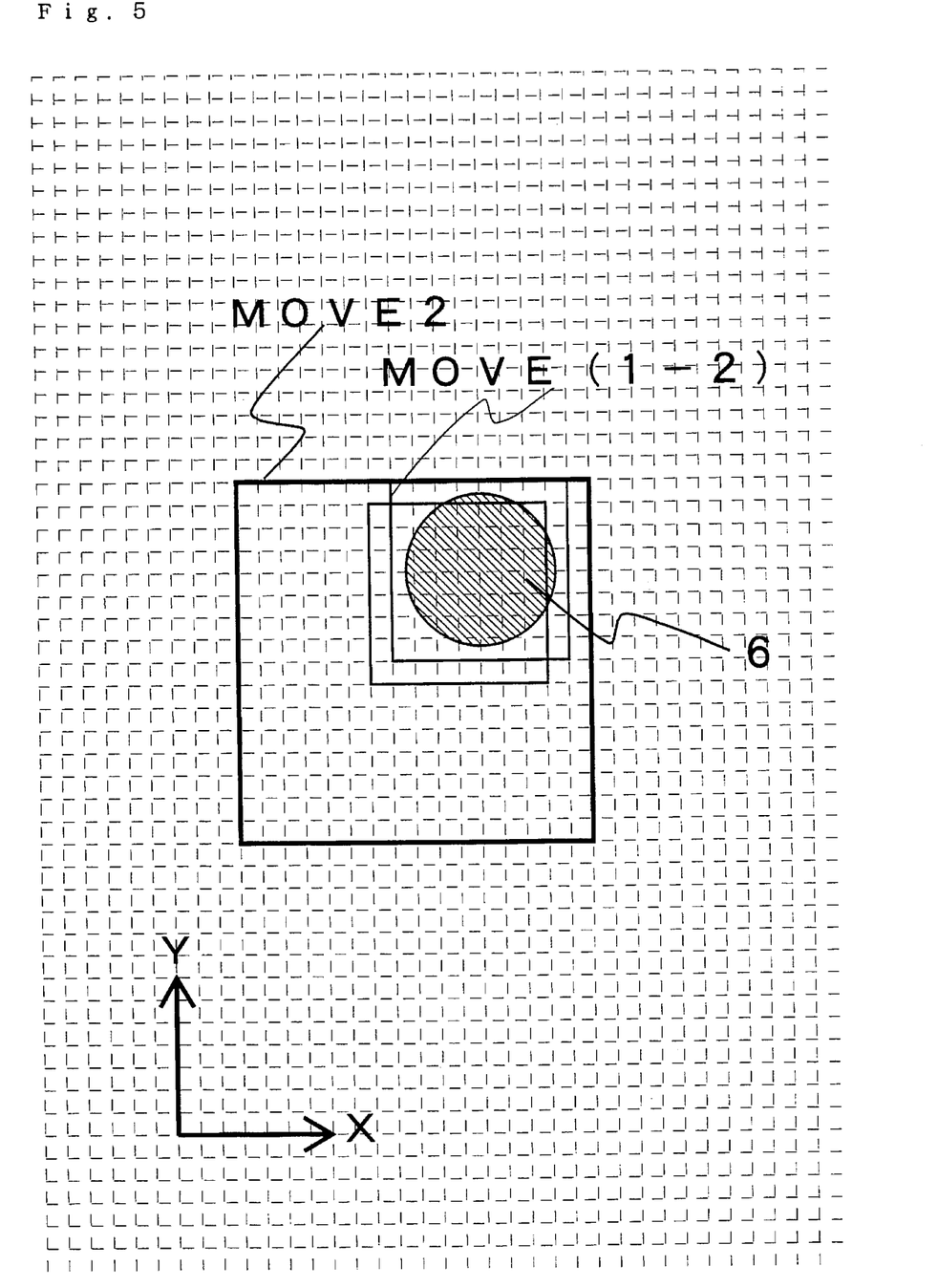
FIG. 5 is still another explanatory view of the motion amount measurement process for laboratory animals according to a method in an embodiment of the present invention.

Thereafter, when the animal 6 further moves, as shown in FIG. 5, the movement amount is counted by recognizing the animal 6 after the movement as a MOVE(1-2) mask. More specifically, the current position and the position of the MOVE(1-1) mask before the movement are compared with each other, and when a movement defined by X=1 and Y=1 is detected, the movement amount is calculated by the following equation:

$$MOVE(1\text{-}2) = \sqrt{(1^2 + 1^2)} = 1.4142 \qquad 2$$

The result of equation 2 is rounded to obtain an amount of "1.4".

The calculation results of the MOVE(I-1) and MOVE(1-2) are added to each other, and data indicating the movement amount of the animal 6 in the state shown in FIG. 5 is "5.0".

Figure 6:
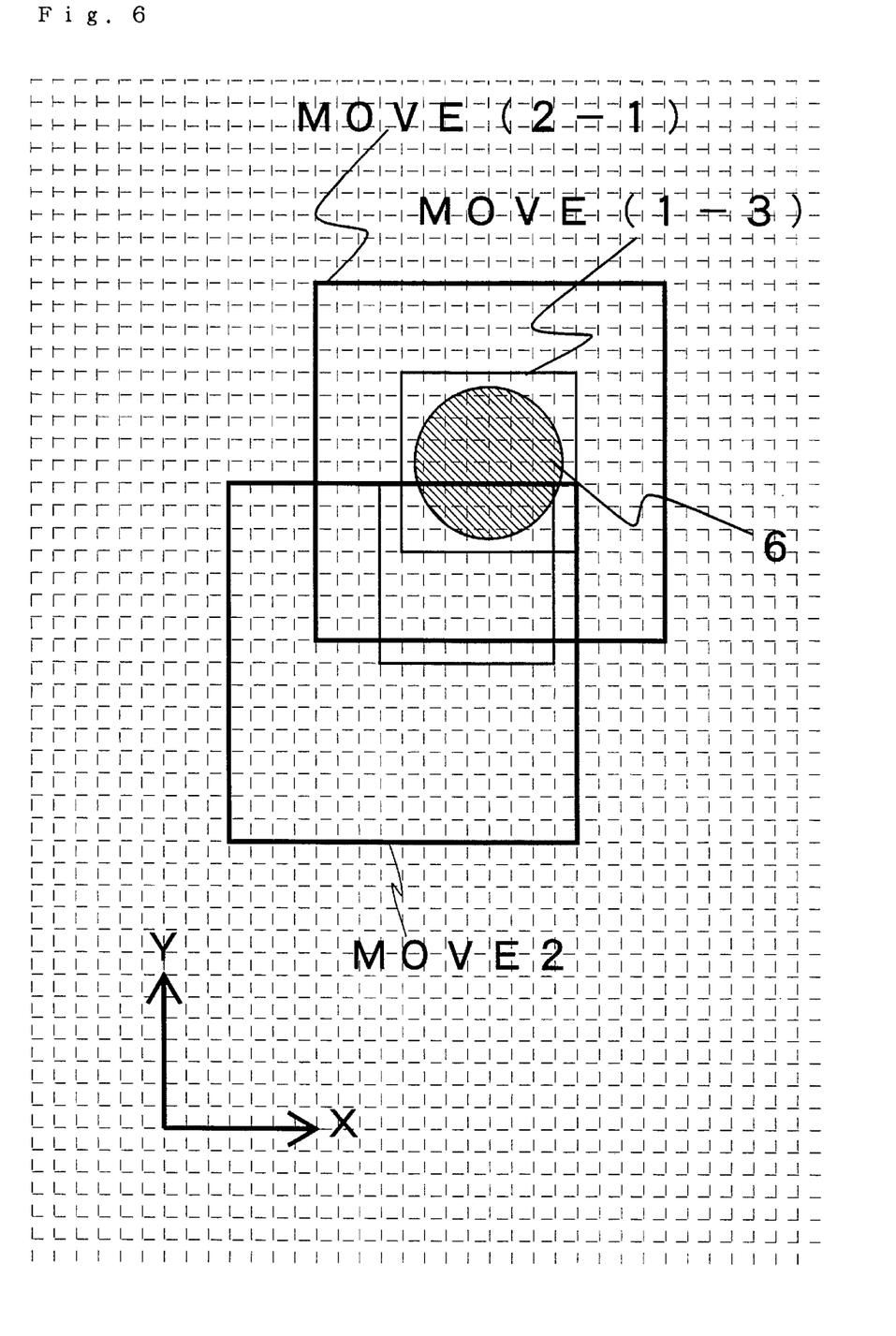
FIG. 6 is still another explanatory view of the motion amount measurement process for laboratory animals according to a method in an embodiment of the present invention.

When the animal 6 further moves to be a state shown in FIG. 6, the positions of a MOVE(1-3) mask and a MOVE(2-1) mask are simultaneously counted. More specifically, the animal 6 after the movement is recognized as the MOVE(1-3) mask, and the recognized position and the position of the MOVE(1-2) mask before the movement are compared with each other. When a movement defined by X=1 and Y=5 is detected, the movement amount is calculated by the following equation:

$$MOVE(1\text{-}3) = \sqrt{(1^2 + 5^2)} = 5.09901 \qquad 3$$

The result of equation 3 is rounded to obtain an amount of "5.1".

The calculation results of MOVE(1-1), MOVE(1-2), and MOVE(1-3) are added to each other, and data indicating the movement amount of the animal 6 in the state shown in FIG. 6 is "10.1".

At the same time, when the animal 6 moves outside a range recognized as the MOVE2 mask as shown in FIG. 6, the animal 6 after the movement is recognized as a new MOVE(2-1) mask, and the position of the MOVE(2-1) mask and the position of the MOVE2 mask before the movement are compared with each other. As a result, when a movement defined by X=4 and Y=9 is detected, the movement amount is calculated using the following equation:

$$MOVE(2\text{-}1) = \sqrt{(4^2 + 9^2)} = 9.8488 \qquad 4$$

The result of equation 4 is rounded to obtain an amount of "9.8".

As described above, the motion amount of the animal 6 is measured by detecting small movements of the animal 6 using the MOVE1 mask. On the other hand, the motion amount is measured by detecting large movements of the animal 6 using the MOVE2 mask. However, the measurement results of the MOVE1 and MOVE2 masks almost coincide with each other.

(2) STANDING ACTION AMOUNT

Figure 7A:
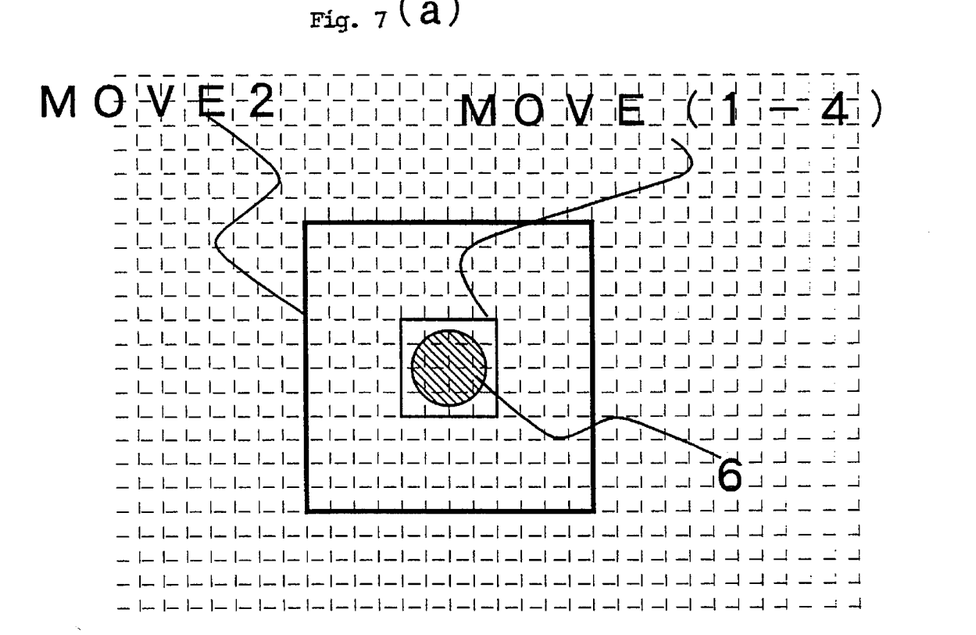
FIG. 7(a) is an explanatory view showing the state detected by sensors when a laboratory animal is in a standing state.
Figure 7B:
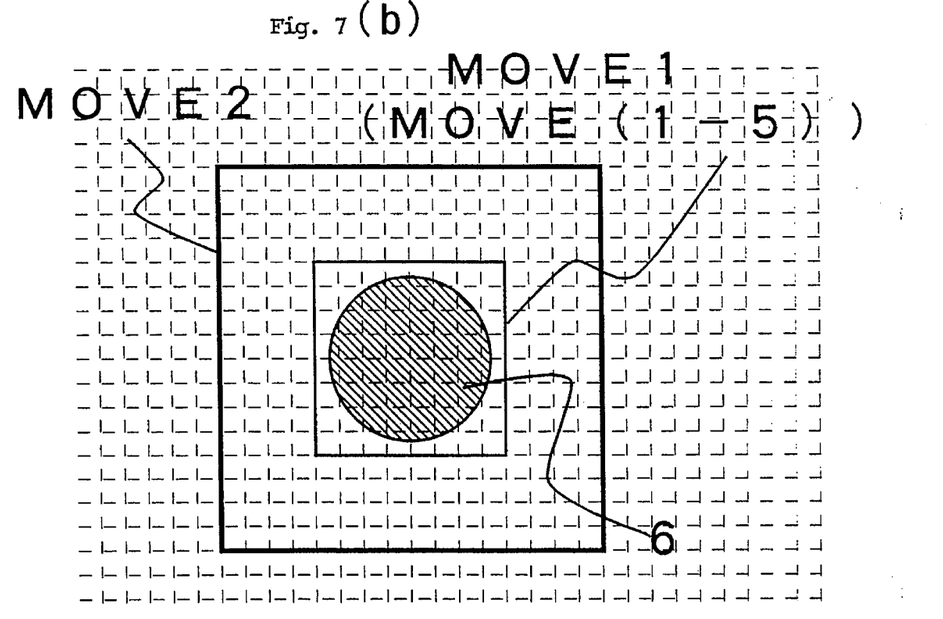
FIG. 7(b) is an explanatory view showing the state detected by sensors when a laboratory animal is in a normal posture.

When an animal takes an action from the normal posture shown in FIG. 8 to a complete standing state on its hind legs, as shown in FIG. 9, since the grounding area of the animal becomes smaller than that in the normal posture, the sizes of the MOVE1 and MOVE2 masks recognized via the optical sensors of the lower frame become smaller, as shown in FIG. 7(a) from those in the normal posture shown in FIG. 7(b). More specifically, the animal 6 in the standing state is recognized as a new MOVE(1-4) mask, and the position of the MOVE(1-4) mask is measured. Then, the position is compared with the position of the MOVE1 mask representing the normal posture. As a result, as shown in FIGS. 7(a) and 7(b), when a reduction defined by X=−4 and Y=−4 is detected, MOVE(1-4) is calculated by the following equation:

$$MOVE(1\text{-}4) = -\sqrt{((-4)^2 + (-4)^2)} = -5.656 \qquad 5$$

The result of equation 5 is rounded to obtain an amount of "−5.7". In addition, the MOVE1 and MOVE2 masks are also recognized via the optical sensors of the upper frame, and the standing state of the laboratory animal is detected.

Thereafter, when the animal returns to the normal posture, the MOVE1 and MOVE2 masks recognized via the optical sensors of the lower frame 3 also return to the state shown in FIG. 7(b). The animal 6 which has returned to the normal posture is recognized as a new MOVE(1-5) mask and the position of the MOVE(1-5) mask is counted to be compared with the position of the MOVE(1-4) mask. As a result, when an enlargement defined by X=4 and Y=4 is detected, MOVE(1-5) is calculated by the following equation:

$$MOVE(1\text{-}5) = \sqrt{(4^2 + 4^2)} = 5.656 \qquad 6$$

The result of equation is rounded to obtain an amount of "5.7".

The return action of the animal from the standing state to the normal posture is recognized by the change from the negative amount in equation 5 to the positive amount in equation 6, thus a single complete standing action of the animal is counted.

In contrast to this, when an animal takes an incomplete standing action, i.e., reaches an incomplete standing state shown in FIG. 10 from the normal posture shown in FIG. 8 and then returns to the normal posture, such a incomplete standing action is detected as follows.

In the incomplete standing state of an animal shown in FIG. 10, the MOVE1 and MOVE2 masks recognized via the optical sensors of the lower frame are reduced in size as shown in FIG. 7(a) as compared to FIG. 7(b) in the normal posture which is similar to the complete standing state, and when the animal returns to the normal posture, the MOVE1 and MOVE2 masks return to the state shown in FIG. 7(b). However, since the posture of the animal is lower than that in the complete standing state, the animal is not detected by the optical sensors of the upper frame. Thus, the number of times of detection of the standing action and the return action to the normal posture by the optical sensors of the lower frame without detecting the standing state by the optical sensors of the upper frame is measured as the number of times of incomplete standing actions.

As described above, according to the present invention, by disposing the optical sensors in a staggered pattern, motion amount measurement can be performed with high accuracy as the tail of an animal is not continuously detected by the optical sensors and only the head, trunk and legs of the animal serve as objects to be measured.

Since the optical sensor light-emitting elements are sequentially electrically scanned to emit optical beams, interferences of light among the optical sensors are prevented causing the optical sensors can be arranged at high density, thus achieving high-accuracy measurement. At the same time, near infrared LEDs and phototransistor as versatile components can be applied as the focusing characteristics and the light-receiving sensitivity of the optical sensors become less important due to the interferences of light among the optical sensors can be ignored, thus providing an inexpensive apparatus.

When detecting the current position of a laboratory animal, since the laboratory animal is detected as the square area, measurements using a plurality of measuring apparatuses can be easily performed and numerical data with high accuracy can be obtained.

By vertically stacking a plurality of frames on which optical sensor light-emitting elements and optical sensor light-receiving elements are arranged, the complete standing actions as well as incomplete standing actions of a laboratory animal can be measured.

What is claimed is:

1. A motion amount measuring method for laboratory animals comprising: stacking a first frame and a second frame in a vertical direction, attaching to each of said first and second frames an optical sensor light-emitting element and an opposing optical sensor light-receiving element, said light-emitting elements emitting optical beams such that said light-emitting elements do not emit beams simultaneously, said light-receiving elements receiving those emitted optical beams which are not obstructed by the laboratory animal so as to detect the location and movements of the laboratory animal, setting the frames to surround a laboratory animal in a bounded area, counting complete standing actions of the animal by detecting a standing state of the animal using said optical sensor light-emitting elements and said optical sensor light-receiving elements arranged on the first frame and by detecting a return action from the standing state to a normal posture of the animal using said optical sensor light-emitting elements and said optical sensor light-receiving elements arranged on the second frame, and counting incomplete standing actions of the animal using said optical sensor light-emitting elements and said optical sensor light-receiving elements arranged on the second frame.

2. A method according to claim 1, wherein the optical sensor light-emitting elements are sequentially electrically scanned to emit optical beams.

3. A method according to claim 2, wherein a length corresponding to an interval between two neighboring optical sensors is added to respective two sides of each of a maximum length and a maximum width of an area of the animal detected by said optical sensor light-emitting elements and said optical sensor light-receiving elements so as to perceive the animal as a square area.

4. A method according to claim 3, wherein the animal is detected by a relatively small area to measure small motion amounts of the animal and the animal is also detected by a relatively large area to measure large motion amounts.

5. A method according to claim 3 or 4, wherein a motion amount δ of the laboratory animal detected as the square area is calculated using the following equation:

$$\delta = \sqrt{(X^2 + Y^2)}$$

wherein X and Y are numeric data representing the lengthwise and breadthwise movements of the square area.

6. A motion amount measuring method as defined in claim 1, wherein said first frame is the upper frame, and the second frame is the lower frame.

* * * * *